US009205134B2

(12) United States Patent
Garcia Quintana et al.

(10) Patent No.: US 9,205,134 B2
(45) Date of Patent: Dec. 8, 2015

(54) USE OF ALPHA-1-ANTITRYPSIN FOR THE PREPARATION OF DRUGS FOR THE TREATMENT OF CHRONIC FATIGUE SYNDROME

(75) Inventors: Ana Garcia Quintana, Barcelona (ES); José Alegre Martin, Barcelona (ES)

(73) Assignee: Grifols, S.A., Barcelona (ES)

( * ) Notice: Subject to any disclaimer, the term of this patent is extended or adjusted under 35 U.S.C. 154(b) by 376 days.

(21) Appl. No.: 12/822,764

(22) Filed: Jun. 24, 2010

(65) Prior Publication Data

US 2010/0331261 A1     Dec. 30, 2010

(30) Foreign Application Priority Data

Jun. 30, 2009   (ES) .................................. 200930387

(51) Int. Cl.
| | | |
|---|---|---|
| *A61K 38/57* | (2006.01) | |
| *A61P 21/00* | (2006.01) | |
| *C07K 14/81* | (2006.01) | |
| *A61K 38/48* | (2006.01) | |
| *A61K 38/56* | (2006.01) | |

(52) U.S. Cl.
CPC ............. *A61K 38/4826* (2013.01); *A61K 38/56* (2013.01); *A61K 38/57* (2013.01); *C07K 14/81* (2013.01)

(58) Field of Classification Search
USPC ......................................................... 435/183
See application file for complete search history.

(56) References Cited

U.S. PATENT DOCUMENTS

| 2,281,222 | A1 | 9/2007 | Grifols |
| 7,291,595 | B2 | 11/2007 | Blanco |
| 7,459,532 | B2 | 12/2008 | Lee et al. |
| 2006/0084598 | A1* | 4/2006 | Blanco ............................ 514/12 |

FOREIGN PATENT DOCUMENTS

| BE | WO2006026837 | * | 3/2006 | ............... C12Q 1/37 |
| EP | 1 656 949 B1 | | 1/2007 | |
| ES | 2281222 A1 | | 9/2007 | |
| WO | WO 00/51623 A2 | | 9/2000 | |
| WO | WO 2004/045634 A1 | | 6/2004 | |
| WO | WO 2005/019434 A2 | | 3/2005 | |
| WO | WO 2008/143633 A2 | | 11/2008 | |
| WO | WO 2009/059082 A2 | | 5/2009 | |

OTHER PUBLICATIONS

Blanco et. al., Medical Hypotheses (2005) 64, 759-769.*
Buchwald et. al., Arch. Intern. Med. (1994) 154, 2049-2053.*
Nijs et. al., Anticancer Research (2005) 25, 1013-1022.*
Englebienne et. al., Clin. Diagn. Lab. Immunol. (Oct. 2005) 12(10): 1259-1260.*
Zamoro et. al., Ann. Pharmacother. (May 2008) 42(5), 640-646.*
Glass, Current Rheumatology Reports (2006) 8, 425-429.*
Blanco et al. (Medical Hypotheses (2005) 64, 759-769).*
Englebienne et al., Clin Diagn Lab Immunol. (Oct. 2005) 12(10): 1259-1260.*
EP Search Report issued Sep. 30, 2010 in corresponding EP 10 38 0071.
Nijs J et al., "Impairments of the 2-5A synthetase/RNase L pathway in chronic fatigue syndrome" In vivo: *International Journal of Experimental and Clinical Pathophysiology and Drug Research, International Institute of Anticancer Research*, GR, vol. 19, No. , (Nov. 1, 2005) pp. 1013-1021.
Office Action issued Jun. 30, 2009 in corresponding Spanish Appln No. 200930387.
The Alpha-1-Antitrypsin Deficiency Registry Study Group, Survival and FEV1 decline in individuals with severe deficiency of alpha-1-antitrypsin, *Am J Respir Crit Care Med* 1998; 158: 49-59.
Afari N, et al., Chronic fatigue syndrome: a review, Am J Psychiatry, 2003; 160(2): 221-236.
American Thoracic Society/European Respiratory Society Statement: Standards for the Diagnosis and Management of Individuals with alpha-1 Antitrypsin Deficiency, *Am J Respir Crit Care Med* (2003); 168: 818-900.
Brantly M., Alpha1-antitrypsin: not just an antiprotease: extending the half-life of a natural anti-inflammatory molecule by conjugation with polyethylene glycol, Am J Respir Cell Mol Biol 2002; 27(6): 652-654.
Craig, T. et al, "Chronic Fatigue Syndrome: Evaluation and Treatment" *American Family Physician*, 15:1083-1090 (2002).
De Meirleir, et al. A 37 kDa 2-5A Binding Protein as a Potential Biochemical Marker for Chronic Fatigue Syndrome, *Am J Med* (2000); 108(2): 99-105.
De Meirleir et al., CFS Etiology, the Immune System, and Infection, *Chronic Fatigue Syndrome: A Biologic Approach*, 201-228 (2002) CRC Press LLC.
Demettre E, et al., Ribonuclease L Proteolysis in Peripheral Blood Mononuclear Cells of Chronic Fatigue Syndrome Patients, J Biol Chem (2002): 20; 277(38): 35746-35751.
Englebienne P, et al., A 37-kDa RNase L: A Novel Form of RNase L Associated with Chromnic Fatigue Syndrome, *Chronic Fatigue Syndrome. A Biological Approach*, CRC Press LLC, (2002) 55-130.
Englebienne P, et al., Interactions between RNase L, ankyrin domain and ABC transporters as a possible origin of pain, ion transport, CNS and immune disorders of chronic fatigue immune dysfunction syndrome, *J Chronic Fatigue Syndrome* (2001); 8 (3/4): 83-102.
Fukuda K, et al., The Chronic Fatigue Syndrome: a Comprehensive Approach to its Definition and Study, *Ann Intern Med.* (1994); 121: 953-959.
Henderson AS., Care-eliciting behavior in man, J Nerv Ment Dis 1974; 159: 172-181.
Hill NF, et al., Natural History of Severe Chronic Fatigue Syndrome, *Arch Phys Med Rehabil* (1999); 80(9): 1090-1094.
Itch N, et al., Cytokine-induced Metallothionine Expression and Modulation of Cytokine Expression by Metallothionine, Yakugaku Zasshi (2007); 127(4): 685-694.
Kratz A, et al., Laboratory Reference Values, *N Engl J Med* (2004); 315(15): 1548-1563.

(Continued)

*Primary Examiner* — Marcela M Cordero Garcia
*Assistant Examiner* — Catherine Mader
(74) *Attorney, Agent, or Firm* — RatnerPrestia

(57) ABSTRACT

The present invention relates to the use of alpha-1-antitrypsin for the preparation of effective drugs for the treatment of chronic fatigue syndrome. In addition, the present invention relates to the use of plasma or other therapeutic forms with an alpha-1-antitrypsin content sufficient to obtain a dose of 6 mg or more of alpha-1-antitrypsin per kg of body weight at a frequency of between 1 and 31 days.

9 Claims, No Drawings

(56) References Cited

OTHER PUBLICATIONS

Kurup RK, et al., Hypothalamic digoxin, Cerebral Chemical Dominance and Myalgic Encephalomyelitis, *Int J Neurosci* (2003); 113(5): 683-701.

The American College of Rheumatology,1990, Criteria for the Classification of Fibromyalgia. Report of the Multicenter Criteria Committee, Arthritis Rheum (1990); 33(2): 160-172.

Lloyd AR, et al., Prevalence of chronic fatigue syndrome in an Australian population, Med J Aug. 1990; 153: 522-528.

Lund-Olesen, L.H. et al. The Etiology and Possible TreatmenT of Chronic Fatigue Syndrome/Fibromyalgia, *Medical Hypotheses* (1994) 43:55-58.

Nijs, J. Chronic Fatigue Syndrome: Exercise Performance Related to Immune Dysfunction *Medicine & Science in Sports & Exercise* (2005) 1647-1654.

Perlmutter DH, et al. The Cellular Defect in Alpha 1-proteinase Inhibitor (alpha 1-PI) deficiency is Expressed in Human Monocytes and in Xenopus Oocytes Injected With Human Liver mRNA, *Proc Natl Acad Sci U S A*, (1985) ; 82(20): 6918-6921.

Rimes KA, et al, Treatments for Chronic Fatigue Syndrome, *Occupational Medicine* (2005): 5(1); 32-39.

Seersholm N, et al., Does alpha-1-antitrypsin Augmentation Therapy Slow the Annual Decline in FEV1 in Patients with Severe Hereditary Alpha-1-antitrypsin Deficiency?, *Eur Respir J* (1997); 10: 2260-2263.

Suhadolnik, et al. Upregulation of the 2-5A synthetase/RNase L antiviral pathway associated with chronic fatigue syndrome, Clin Infect Dis 1994; 18 (Suppl. I): S96-S104 (1994).

Tarello, W. Chronic Fatigue Syndrome (CFS) Associated with *Staphylococcus* spp. Bacteremia, Responsive to Potassium Arsenite 0.5% in a Veterinary Surgeon and His Coworking Wife, Handling with CFS Animal Cases, *Comparative Immunology, Microbiology & Infectious Diseases*, 24:233-246 (2001).

Wencker M, et al., Long term Treatment of alpha-1-antitrypsin Deficiency-related Pulmonary Emphysema with Human alpha-1-antitrypsin, *Eur Respir J* (1998); 11: 428-433.

Wewers MD, et al., Replacement therapy for alpha1-antitrypsin deficiency associated with emphysema, New Eng J Med 1987; 316: 1055-1062.

White PD, et al., Protocol for the PACE trial: a randomised controlled trial of adaptive pacing, cognitive behaviour therapy, and graded exercise, as supplements to standardised specialist medical care versus standardised specialist medical care alone for patients with the chronic fatigue syndrome/myalgic encephalomyelitis or encephalopathy, *BMC Neurol* (2007), 7: 6.

Zhang B, et al., Alpha1-antitrypsin Protects beta-cells From Apoptosis, Diabetes (2007); 56(5): 1316-1323.

The Royal Australasian College of Physicians. Chronic Fatigue Syndrome. Clinical Practice Guidelines 2002; (2002) pp. S17-S56.

Fregonese et al., "Hereditary Alpha-1-Antitrypsin Deficiency and its Clinical Consequences" Orphanet Journal of Rare Diseases, (2008), vol. 3, No. 16, pp. 1-9.

Malashenkov et al., Jun. 17, 1997, vol. 5, No. 12, 4 Pages.

Examination Report dated Jun. 11, 2010, issued in the corresponding New Zealand Patent Application No. 585890.

Office Action dated Apr. 14, 2011, issued in the corresponding Russian Patent Application No. 2010126653, and an English Translation thereof.

\* cited by examiner

USE OF ALPHA-1-ANTITRYPSIN FOR THE PREPARATION OF DRUGS FOR THE TREATMENT OF CHRONIC FATIGUE SYNDROME

The present invention relates to the use of alpha-1-antitrypsin for the preparation of effective drugs for the treatment of chronic fatigue syndrome.

BACKGROUND

Chronic fatigue syndrome (CFS) is a complex disorder, defined by the international Fukuda criteria (Fukuda K, et al., The chronic fatigue syndrome: a comprehensive approach to its definition and study, Ann Intern Med. 1994; 121: 953-959) under the supervision of the Atlanta Center for Disease Control (CDC). According to these criteria, the diagnosis of CFS is based on two major criteria being met and the coexistence of a minimum of four minor criteria.

Major Criteria

1. Persistent physical and mental fatigue for at least six months, or of an intermittent character, of new or definite onset, which does not result from recent efforts, is not alleviated by rest, and gets worse with activity, and which causes a substantial reduction in the patient's previous levels of daily activity, which ultimately the patient cannot overcome.

2. Exclusion of other disorders which may potentially cause chronic fatigue, such as endocrine, infectious, neoplastic and/or psychiatric disorders.

Minor Criteria

Four or more of the following minor criteria must be present concurrently, all lasting for six months or more after the presentation of fatigue:

Impairment in concentration or short-term memory.
Odynophagia.
Painful cervical or axillary adenopathies.
Myalgia.
Polyarthralgia with no signs of inflammation.
Headaches of recent onset or with characteristics different from usual.
Unrefreshing sleep.
Post-exertion malaise lasting more than 24 hours.

Among the disorders that may be confused with CFS is fibromyalgia (FM), which is a syndrome characterised by symptoms of chronic generalised musculoskeletal pain that is not articular in origin. According to the classification criteria of the American College of Rheumatology (The American College of Rheumatology, 1990, Criteria for the Classification of Fibromyalgia. Report of the Multicenter Criteria Committee, Arthritis Rheum 1990; 33(2): 160-172) the two basic characteristics for the diagnosis of FM are:

1) the presence of generalised pain lasting over three months;

2) abnormal sensitivity to digital pressure of approximately 4 kg in at least 11 of 18 specific points, known as "tender points". Besides pain, patients with FM experience some of the following symptoms: sleep disorders, irritable bowel syndrome, ankylosis and stiffness, head or face aches, abdominal malaise, irritable bladder, paraesthesia, numbness or itching, chest pains and costochondralgia (muscle pain where the ribs join the sternum), dizziness and nausea, etc. Symptoms tend to fluctuate and do not necessarily occur simultaneously.

FM and CFS are two different disorders but with very similar presentation and symptoms, this frequently confusing non-experts, despite which, they may coexist in many patients. Almost 80% of CFS sufferers meet the FM classification criteria, although only 7 to 10% of patients with FM meet those for CFS. Differential diagnosis between the two and eliminating other possible causes of pain and fatigue is fundamental for a correct diagnostic, prognostic and therapeutic approach.

CFS predominantly affects young adults with an onset peak between 20 and 40 years. It is 2-3 times more common in women than in men (Lloyd A R, et al., Prevalence of chronic fatigue syndrome in an Australian population, Med J August 1990; 153: 522-528), although this ratio may be due to women seeking medical care at all levels more frequently (Henderson A S., Care-eliciting behavior in man, J Nery Ment Dis 1974; 159: 172-181).

The prevalence of CFS in the population is between 0.4 and 2.5% (White P D, et al., Protocol for the PACE trial: a randomised controlled trial of adaptive pacing, cognitive behaviour therapy, and graded exercise, as supplements to standardised specialist medical care versus standardised specialist medical care alone for patients with the chronic fatigue syndrome/myalgic encephalomyelitis or encephalopathy, BMC Neurol 2007, 7: 6). In the United States and the United Kingdom, four studies give an estimate of 0.2% to 0.7%, in other words, 200 to 700 cases per 100,000 people. In Japan, a prevalence of 1.5% was recorded. In general, prevalence estimates for CFS were between 0.5% and 2.5% in primary care centres, depending on the intensity of medical, psychiatric and laboratory evaluation (The Royal Australasian College of Physicians. Chronic Fatigue Syndrome. Clinical Practice Guidelines 2002).

The prognosis for recovery from CFS is extremely poor and at present there is no universal treatment which has been demonstrated to be an effective option for treating CFS (Hill N F, et al., Natural history of severe chronic fatigue syndrome, Arch Phys Med Rehabil 1999; 80(9): 1090-1094). Therefore, as things stand, the main therapeutic objective is based on alleviating the symptoms. Some of the treatments offered include: cognitive behavioural therapy, graduated exercise therapy, pharmacological intervention (such as antiviral, antidepressant, sedative, analgesic, anti-inflammatory and other drugs) and nutritional supplements. However, these interventions often do not produce the minimum benefit considered necessary in many patients with CFS (Afari N, et al., Chronic fatigue syndrome: a review, Am J Psychiatry, 2003; 160(2): 221-236/Rimes K A, et al, Treatments for Chronic Fatigue Syndrome, Occupational Medicine 2005: 5(1); 32-39). It is therefore clear that there is a need for effective medicines for the treatment of CFS.

CFS is a multisystemic disease of which the aetiology or triggering factor is not known, although there are various hypotheses as to the causal agents: genetic defects, abnormalities of the central nervous system, neuromuscular and metabolic irregularities, psychological factors, toxic agents, infections and immunological imbalances due to chronic activation of the immune system (Afari N, et al., Chronic fatigue syndrome: a review, Am J Psychiatry, 2003; 160(2): 221-236). Specifically, based on the chronically activated immune state, some authors suggested that the clinical and immunological abnormalities observed in CFS could include defects in the 2-5A defence pathway induced by interferons (Englebienne P, et al., Chronic Fatigue Syndrome. A Biological Approach, CRC Press LLC, 2002).

Interferons (IFNs) are proteins produced naturally by the immune system in response to external agents such as bacteria, viruses and parasites, and cancer cells. The two most significant products for IFN stimulation are the protein kinase R (PKR) and ribonuclease L (RNase L). PKR inhibits the translation of viral mRNA whereas RNase L shuts off dsRNA. The ultimate objective of both proteins is to induce the apoptosis of the infectious agents.

In 1994 Suhadolnik, et al. (Upregulation of the 2-5A synthetase/RNase L antiviral pathway associated with chronic fatigue syndrome, Clin Infect Dis 1994; 18 (Suppl. I): S96-S104) discovered that the peripheral blood mononuclear cells (PBMC) of patients with CFS had hyperactive RNase L with a molar mass of 37 kDa, produced by the proteolysis of the native form of 83 kDa RNase L. Later, De Meirleir, et al. (A 37 kDa 2-5A binding protein as a potential biochemical marker for chronic fatigue syndrome, Am J Med 2000; 108 (2): 99-105) observed that the ratio between the concentration of the 37 kDa molecule and the 83 kDa molecule in PBMC was useful for differentiating patients with CFS from those suffering from FM or major depression.

Patients with CFS exhibit many symptoms which are characteristic of ion channel transport dysfunctions. The potential for ion channel interruption in patients with CFS was taken into account when it was determined that the RNase L inhibitor (RLI) belonged to the ABC superfamily of ion channel transporters. RLI deactivates RNase L by combining with the ankyrin domains present in RNase L. The elimination of the ankyrin domain during RNase L fragmentation, seen in patients with CFS, suggested that these ankyrin fragments may be capable of interacting and interrupting the normal functioning of the ion channels. A dysfunction of these transporters would explain many of the symptoms found in patients with CFS: nocturnal sweats, sarcoidosis, chemical hypersensitivity, macrophage dysfunction, immune system deficiency, disrupted monoamine transport, increased sensitivity to pain, Th2 dominance, abnormalities of the central nervous system, vision problems, loss of potassium in the muscles, transitory hypoglycaemia and depression (Englebienne P, et al., Interactions between RNase L, ankyrin domain and ABC transporters as a possible origin of pain, ion transport, CNS and immune disorders of chronic fatigue immune dysfunction syndrome, J Chronic Fatigue Syndrome 2001; 8 (3/4): 83-102).

Elastase, cathepsin-G and m-calpain are enzymes capable of causing the proteolysis or fragmentation of RNase L (Englebienne P, et al., Interactions between RNase L, ankyrin domain and ABC transporters as a possible origin of pain, ion transport, CNS and immune disorders of chronic fatigue immune dysfunction syndrome, J Chronic Fatigue Syndrome 2001, 8 (3/4): 83-102/Demetre E, et al., Ribonuclease L proteolysis in peripheral blood mononuclear cells of chronic fatigue syndrome patients, J Biol Chem 2002: 20; 277(38): 35746-35751). These three proteases are involved in the defence mechanisms against pathogenic agents and in the inflammatory processes, and they are therefore often found in abnormally high concentrations during an inflammatory response. In the case of CFS, it was found that patients suffering from this disorder usually had high concentrations of elastase (Demetre E, et al., Ribonuclease L proteolysis in peripheral blood mononuclear cells of chronic fatigue syndrome patients, J Biol Chem 2002: 20; 277(38): 35746-35751/Nijs J, et al. Chronic fatigue syndrome: exercise performance related to immune dysfunction, Med Sci Sports Exerc 2005; 37(10): 1647-1654).

Demetre E, et al. demonstrated that elastase has a significant role in the degradation of RNase L, when they proved that a specific inhibitor of elastase was capable of inhibiting, to a great extent, the proteolysis of RNase L in a PBMC culture from patients with CFS.

Faced with the need to find effective drugs for the treatment of CFS, the inventors undertook very extensive, in-depth investigations and tests which have resulted in the present invention, which is based on the use of alpha-1-antitrypsin (AAT) for the preparation of drugs for the treatment of CFS.

DESCRIPTION OF THE INVENTION

Alpha-1-antitrypsin (AAT) is a glycoprotein secreted in hepatocytes, and is normally present in high concentrations in serum and in most tissues, where it acts as a serine protease inhibitor. The reference values for AAT in the serum of healthy subjects are 0.83-2.00 g/l (Kratz A, et al., Laboratory Reference Values, N Engl J Med 2004; 315(15): 1548-1563). Apart from its activity as a protease inhibitor, AAT has been described as possibly having an important anti-inflammatory biological function, as it has a significant capacity to inhibit many inflammation mediators and oxidising radicals (Brantly M., Alpha1-antitrypsin: not just an antiprotease: extending the half-life of a natural anti-inflammatory molecule by conjugation with polyethylene glycol, Am J Respir Cell Mol Biol 2002; 27(6): 652-654).

AAT deficiency is a hereditary disease which primarily causes pulmonary emphysema in the early stages of adult life (30-40 years). The second most frequent manifestation is liver disease, which may affect newborns, children and adults. Less frequent is an inflammatory skin disease known as necrotising panniculitis (American Thoracic Society/European Respiratory Society Statement: Standards for the diagnosis and management of individuals with alpha-1 antitrypsin deficiency, Am J Respir Crit Care Med 2003; 168: 818-900).

At present, therapeutic AAT concentrates exist, prepared by the fractionation of human blood plasma, which is used in AAT replacement therapy for the treatment of subjects with a deficiency of this protein and associated pulmonary emphysema. These concentrates have been shown to be biochemically effective in raising the serum concentration of AAT above the minimum levels considered protective (11 μmol/l) (Wewers M D, et al., Replacement therapy for alpha1-antitrypsin deficiency associated with emphysema, New Eng J Med 1987; 316: 1055-1062). In addition, various clinical studies suggest that AAT replacement therapy is clinically effective in slowing the progression of pulmonary emphysema and reducing mortality (Seersholm N, et al., Does alpha-1-antitrypsin augmentation therapy slow the annual decline in FEV1 in patients with severe hereditary alpha-1-antitrypsin deficiency?, Eur Respir J 1997; 10: 2260-2263/The Alpha-1-Antitrypsin Deficiency Registry Study Group, Survival and FEV1 decline in individuals with severe deficiency of alpha-1-antitrypsin, Am J Respir Crit Care Med 1998; 158: 49-59).

Extensive clinical experience in AAT replacement therapy confirms that therapeutic concentrates of AAT originating from human plasma have an excellent safety profile (Wencker M, et al., Long term treatment of alpha-1-antitrypsin deficiency-related pulmonary emphysema with human alpha-1-antitrypsin, Eur Respir J 1998; 11: 428-433/American Thoracic Society/European Respiratory Society Statement: Standards for the diagnosis and management of individuals with alpha-1 antitrypsin deficiency, Am J Respir Crit Care Med 2003; 168: 818-900).

To check whether the inhibition of elastase by AAT could prevent RNase L degradation, the inventors carried out various studies using in vitro PBMC culture from patients with CFS together with AAT concentrates. Based on these studies, the inventors established that PBMC extracts from patients with CFS show raised elastase activity, far higher than that of PBMC extracts from healthy subjects. PBMC extracts from six healthy subjects showed an average elastase activity of 81

U/mg of extract (CV=38.9), with a minimum-maximum of 51-125 U/mg of extract, whereas the PBMC extracts from eight patients with CFS exhibited an average elastase activity of 322 U/mg of extract (CV=30.5), with a minimum-maximum of 193-453 U/mg of extract.

The inventors also discovered that AAT was capable of substantially inhibiting the intracellular elastase activity of cultures of PBMC from patients with CFS. The PBMCs of 10 patients with CFS were cultured for 12 hours in the absence and in the presence of two different concentrations of AAT: 3 g/l and 6 g/l. The results obtained for the inhibition percentage of elastase activity in the control with no AAT were as follows: for the 3 mg/ml AAT culture, intracellular elastase activity was inhibited by an average of −87.2% (CV=0.09), with a minimum-maximum of −75.3 to −95.4%; for the 6 mg/ml AAT culture, intracellular activity was inhibited by an average of −91.0% (CV=0.08), with a minimum-maximum of −76.1 to 97.4%.

In addition, the inventors established that AAT prevented degradation of 83 kDa RNase L, to generate the hyperactive form of 37 kDa RNase L, in PBMC cultures from patients with CFS. The PBMCs of two healthy subjects and the PBMCs of two patients with CFS were cultured for 12 hours in the absence and in the presence of 3 g/l of AAT. In the PBMC cultures of the two healthy subjects, no significant differences were observed in the analysis of RNase L degradation between the two cultures. Following the culture of PBMC without AAT, the ratio of 83 kDa RNase L to 37 kDa RNase L was 0.3 and 0.4 whereas following culture with AAT, the ratio of 83 kDa RNase L to 37 kDa RNase L was 0.2 and 0.3, respectively. Both values were below the limit of 0.5 regarded as marking proteolysis of 83 kDa RNase L. In PBMC cultures from patients with CFS, it was found that in the presence of AAT, RNase L degradation diminished by 80%. Following PBMC culture with no AAT from the two patients with CFS, the ratio of 83 kDa RNase L to 37 kDa RNase L was 1.4 and 2.4 whereas following culture with AAT, the ratio of 83 kDa RNase L to 37 kDa RNase L was 0.2 and 0.6, respectively.

The present inventors found that AAT activated the expression of genes involved in the 2-5A synthetase pathway so that the administration of exogenous AAT could re-establish normal RNase L activity and prevent its proteolysis in the PBMCs of patients with CFS.

The PBMCs of six patients with CFS were cultured in the absence and in the presence of two different concentrations of AAT: 0.5 g/l and 3.0 g/l. Next, the RNA was extracted and analysed with the Genechips Human Genome U133 Plus 2.0 (Affymetrix) system. The expression of the gene coding for 2,5-oligoadenylate synthetase, the enzyme responsible for the synthesis of 2-5A molecules, and therefore RNase L activators, increased 2.9 and 3.2 times in cultures with 0.5 g/l and 3.0 g/l AAT respectively, compared with cultures in the absence of AAT. Therefore, stimulation of the expression of 2,5-oligoadenylate synthetase by AAT, could re-establish the activity of RNase L itself and at the same time help prevent its proteolysis.

The inventors also found that AAT inhibited the expression of metallothionines, and therefore the administration of exogenous AAT could reduce activation of the proinflammatory pathways of the PBMCs of patients with CFS. The PBMCs of six patients with CFS were cultured in the absence and in the presence of two different concentrations of AAT: 0.5 g/l and 3.0 g/l. Next, the RNA was extracted and analysed with the Genechips Human Genome U133 Plus 2.0 (Affymetrix) system. The results were presented as the ratio between the expression of genes in the presence of AAT compared with the expression of genes in the absence of AAT. The expression of various genes coding for metallothionines reduced following cultures in the presence of AAT. Specifically, the expression of metallothionine 2A, metallothionine 1X, metallothionine 1H, metallothionine 1F and metallothionine 1E diminished on average 2.2 and 4.5 times in cultures with 0.5 g/l and 3.0 g/l AAT respectively compared with cultures in the absence of AAT. As described, a metallothionine deficiency reduces the production of proinflammatory cytokines (IL1b, IL6, TNFa) (Itoh N, et al., Cytokine-induced metallothionine expression and modulation of cytokine expression by metallothionine, Yakugaku Zasshi 2007; 127(4): 685-694). Thus, the inhibition of expression caused by AAT could produce the same effect and reduce the proinflammatory pathways in PBMCs. In addition, metallothionines also play a very important role in the production of nitric oxide (NO), an immune mediator present in raised concentrations in patients with CFS (Kurup R K, et al., Hypothalamic digoxin, cerebral chemical dominance and myalgic encephalomyelitis, Int J Neurosci 2003; 113(5): 683-701). A fall in NO production, due to a reduction in the expression of metallothionines induced by AAT could be another beneficial action of this protein in the context of patients with CFS.

The inventors also found that AAT activated the expression of the gene coding for AAT, so that the administration of exogenous AAT could promote its own expression in the PBMCs of patients with CFS. The PBMCs of six patients with CFS were cultured in the absence and in the presence of two different concentrations of AAT: 0.5 g/l and 3.0 g/l. Next, the RNA was extracted and analysed with the Genechips Human Genome U133 Plus 2.0 (Affymetrix) system. The results were presented as the ratio between the expression of genes in the presence of AAT compared with the expression of genes in the absence of AAT. The expression of the gene coding for AAT (SERPINA1) increased 1.4 and 2.0 times on average in cultures with 0.5 g/l and 3.0 g/l AAT respectively, compared with cultures in the absence of AAT. Although AAT is synthesised mainly in the hepatocytes, Perlmutter D H, et al. also described their expression in monocytes (The cellular defect in alpha 1-proteinase inhibitor (alpha 1-PI) deficiency is expressed in human monocytes and in *Xenopus* oocytes injected with human liver mRNA, Proc Natl Acad Sci USA, 1985; 82(20): 6918-6921). Therefore, AAT expressed intracellularly and induced by the presence of AAT could have an inhibiting effect on the elastase of the PBMC cultures of patients with CFS. Furthermore, it cannot be discounted that AAT may directly inhibit intracellular elastase after being internalised in PBMC cells, as described for other types of cells (Zhang B, et al., Alpha1-antitrypsin protects beta-cells from apoptosis, Diabetes 2007; 56(5): 1316-1323). Therefore, the two elastase inhibiting mechanisms in PBMC cultures from patients with CFS could coexist and even produce a cumulative effect.

These discoveries are even more surprising since the potential new therapeutic applications of drugs containing AAT originating from these experiments could in no way be related to the applications of this protein known hitherto which were based strictly on compensation of the natural deficiency presenting as pulmonary diseases (pulmonary emphysema) or inflammatory skin disorders (panniculitis).

Although the inventors do not wish to feel limited to any hypothesis as to the form manifested by new drugs containing AAT in the treatment of CFS, they have established, in a non-limiting manner, the hypothesis that AAT has an important role in the control of the immunological cells responsible for the symptoms associated with CFS, and in the regulation of the expression of genes related to the immunological system.

CFS may be treated with therapeutic concentrates of AAT, purified from human plasma or produced by recombinant or transgenic technology. Treatment is also possible with plasma or other therapeutic products containing a sufficient quantity of AAT to obtain a minimum dose.

As occurs with other proteins, the presence of the complete AAT molecule is not thought to be necessary to obtain the required result. Thus, molecules containing a partial sequence of amino acids derived from the corresponding sequence of the AAT molecule may be of use for the treatment of CFS. These molecules may be obtained from human plasma or produced by synthetic methods or by recombinant or transgenic technology.

The present invention also relates to a method for the treatment of CFS which comprises the administration of a therapeutically effective quantity of AAT, in combination with one or more pharmaceutically inert or active carriers, to a patient suffering from or with a risk of developing CFS.

The treatment regime according to the invention includes the periodic and repeated administration of AAT for the purpose of reducing or eliminating the symptoms of CFS. A dose of 6 mg or more of AAT per kilogram (kg) of body weight infused at a frequency of between 1 and 31 days is considered sufficient for the treatment of CFS. A preferred dose of AAT would be between 15 and 360 mg per kg of body weight infused at a frequency of between 1 and 31 days. An even more preferred dose would be between 25 and 60 mg per kg of body weight every week or multiples of these quantities adjusted proportionally depending on the expected time interval until the next dose.

Alternatively, the present invention includes a treatment regime established to achieve a desired level of AAT in the serum up to eight times higher than the base levels, 24 hours after administration.

According to the embodiment of the invention, AAT may be administered by parenteral injection and according to a preferred embodiment, administration takes place intravenously, although it may also be administered intramuscularly or intradermally. Alternatively, AAT may be administered by inhalation. Depending on the administration route, the preparation of AAT is made up as a solution or suspension in a pharmaceutically acceptable vehicle or carrier. Appropriate examples of such vehicles include: water for injection, sterile water for injection and other aqueous vehicles (for example, injectable sodium chloride, injectable Ringer's solution, injectable dextrose, injectable dextrose and sodium chloride, injectable Ringer's lactate); vehicles which can be mixed in water (for example, ethyl alcohol, polyethylene alcohol, glycol propylene); non-aqueous vehicles (for example, corn oil, cottonseed oil, peanut oil and sesame oil). The need for and selection of other excipients, preservatives, buffer solutions, biocides and similar products are within the scope of persons skilled in the art and will depend on various factors, including the administration system and route, the required shelf life and the storage and transport conditions.

EXAMPLE

While waiting for the results obtained in vitro, the inventors, having been granted a compassionate use authorisation, administered a preparation based on AAT to a patient diagnosed with CFS.

A female patient was diagnosed with CFS in 2003 having met the Fukuda diagnostic criteria, and other medical processes inducing chronic fatigue, such as endocrine, infectious, neoplastic and/or psychiatric disorders having been ruled out. Before beginning treatment with AAT concentrate, the patient had an elastase concentration in PBMC of 1459 U/mg (units of activity per milligram of PBMC extract); in the functional reserve assessment test, the patient exhibited a maximum oxygen consumption of 17.2 ml/kg/min (63.5% of theoretical), a maximum power of 64 watts (54.0% of theoretical), a maximum heart rate of 149 beats (87.6% of theoretical); and in the neurocognitive dysfunction study, showed very serious cognitive impairment. The patient was subjected to therapy with intravenous infusions of the AAT-based preparation (60 mg/kg of body weight weekly) for a period of eight weeks. At the end of the treatment, the patient exhibited an elastase concentration in PBMC of 134 U/mg (units of activity per milligram of PBMC extract); in the functional reserve assessment test, the patient exhibited a maximum oxygen consumption of 16.4 ml/kg/min (60.6% of theoretical), maximum power of 85 watts (71.7% of theoretical), a maximum heart rate of 151 beats (88.8% of theoretical); and in the neurocognitive dysfunction study displayed serious cognitive impairment. As a general conclusion, after treatment with the AAT-based preparation, the patient showed clear clinical improvement, she returned to work, experienced less fatigue and exhibited improved tolerance of physical exercise and slightly reduced cognitive dysfunction.

It is therefore demonstrated that by means of the present invention, patients with CFS can be effectively treated with drugs prepared on the basis of AAT. These patients would be affected by chronic inflammation of immunological cells and, according to the present invention, AAT inhibits elastase and thus avoids RNase L degradation, so preventing ion channel deregulation, which is supposedly responsible for the symptomology associated with CFS. In addition, and according to the results obtained in vitro, AAT could regulate the expression of particular genes associated with the immunological system to re-establish normal functioning of the immunological system and reduce activation of the proinflammatory pathways.

Although the invention has been described in relation to examples of preferred embodiments, these should not be considered as limiting the invention, which is defined by the widest interpretation of the following claims.

The invention claimed is:

1. A method for treating cognitive impairment in a patient suffering from chronic fatigue syndrome comprising administering to said patient alpha-1-antitrypsin at a dose sufficient to reduce said cognitive impairment.

2. The method of claim 1, wherein the dose of alpha-1-antitrypsin is sufficient to reduce the ratio of 83 kDa RNase L to 37 kDa RNase L below 0.5 as measured in peripheral blood mononuclear cells from said patient.

3. The method of claim 1, wherein administering to said patient alpha-1-antitrypsin at a dose sufficient to reduce said cognitive impairment comprises administering to said patient alpha-1-antitrypsin at a dose greater than 6 mg/kg patient body weight.

4. The method of claim 3, wherein the dose of alpha-1-antitrypsin administered to said patient is 15-360 mg/kg patient body weight.

5. The method of claim 3, wherein administration of the dose of alpha-1-antitrypsin is repeated at least once at a frequency between 1 and 31 days.

6. The method of claim 1, wherein the alpha-1-antitrypsin is administered at a dose sufficient to achieve a level of alpha-1-antitrypsin in serum of the patient up to eight times higher than base levels, 24 hours after administration.

7. The method of claim 1, wherein administering to said patient alpha-1-antitrypsin at a dose sufficient to reduce said cognitive impairment comprises administering to said patient alpha-1-antitrypsin at a dose ranging from 25 to 60 mg/kg patient body weight, and the dose is repeated at least once at a frequency of 1 week.

8. The method of claim 1, wherein administering to said patient alpha-1-antitrypsin is performed by a route selected from the group consisting of: parenterally, intravenously, intramuscularly, intradermally, and inhalation.

9. The method of claim 1, wherein administering to said patient alpha-1-antitrypsin at a dose sufficient to reduce said cognitive impairment comprises administering to said patient alpha-1-antitrypsin at a dose ranging from 25 to 60 mg/kg patient body weight, and the dose is repeated at least once at a frequency of 1 week for a period of 8 weeks.

* * * * *